(12) United States Patent
Oliver et al.

(10) Patent No.: US 8,313,762 B2
(45) Date of Patent: Nov. 20, 2012

(54) FLEXIBLE BIORESORBABLE HEMOSTATIC PACKING AND STENT

(75) Inventors: Dana A. Oliver, Jacksonville, FL (US); Matthew J. Halvorsen, Hopkinton, NH (US); Aimee Hodge, Candia, NH (US)

(73) Assignee: Medtronic Xomed, Inc., Jacksonville, FL (US)

( * ) Notice: Subject to any disclaimer, the term of this patent is extended or adjusted under 35 U.S.C. 154(b) by 951 days.

(21) Appl. No.: 11/482,234

(22) Filed: Jul. 5, 2006

(65) Prior Publication Data

US 2008/0008738 A1    Jan. 10, 2008

(51) Int. Cl.
*A61F 2/02* (2006.01)
*A61K 31/17* (2006.01)

(52) U.S. Cl. .......................................... 424/426; 514/57
(58) Field of Classification Search .................. 424/426
See application file for complete search history.

(56) References Cited

U.S. PATENT DOCUMENTS

| | | | | |
|---|---|---|---|---|
| 2,914,444 A * | 11/1959 | Smith | | 424/423 |
| 3,005,457 A * | 10/1961 | Millman et al. | | 604/368 |
| 4,292,972 A | 10/1981 | Pawelchak et al. | | 128/296 |
| 5,017,229 A | 5/1991 | Burns et al. | | 106/162 |
| 5,336,163 A | 8/1994 | DeMane et al. | | 602/46 |
| 5,422,068 A * | 6/1995 | Shalaby et al. | | 422/22 |
| 6,923,961 B2 * | 8/2005 | Liu et al. | | 424/94.64 |
| 2003/0187381 A1 * | 10/2003 | Greenawalt et al. | | 604/11 |
| 2003/0202970 A1 * | 10/2003 | Liu et al. | | 424/94.64 |
| 2004/0116958 A1 | 6/2004 | Gopferich et al. | | 606/199 |
| 2005/0058632 A1 * | 3/2005 | Hedrick et al. | | 424/93.7 |
| 2005/0123588 A1 * | 6/2005 | Zhu et al. | | 424/443 |
| 2005/0260188 A1 * | 11/2005 | Liu et al. | | 424/94.64 |
| 2006/0057182 A1 | 3/2006 | Oliver et al. | | 424/423 |
| 2006/0121086 A1 * | 6/2006 | Boyer et al. | | 424/426 |
| 2007/0259029 A1 * | 11/2007 | McEntire et al. | | 424/449 |
| 2008/0008738 A1 * | 1/2008 | Oliver et al. | | 424/426 |
| 2008/0031929 A1 * | 2/2008 | Baggett | | 424/443 |

OTHER PUBLICATIONS

Barbucci, et. al., "Swelling Behavior of Carboxymethylcellulose Hydrogels in Relation to Cross-Linking, pH, and Charge Density", Macromolecules, 2000, vol. 33, pp. 7475-7480.*
Ershov (Russ.Chem.Rev., 67, (4), pp. 315-334, 1998).*
Sintzel, Drug Development and Industrial Pharmacy, 23, 1997.*

\* cited by examiner

*Primary Examiner* — Robert A Wax
*Assistant Examiner* — William Craigo
(74) *Attorney, Agent, or Firm* — Dicke, Billig & Czaja, PLLC

(57) ABSTRACT

The invention provides a flexible bioresorbable foam having hemostatic properties. The foam is formed from a carboxymethylcellulose suspension.

17 Claims, No Drawings

FLEXIBLE BIORESORBABLE HEMOSTATIC PACKING AND STENT

THE FIELD OF THE INVENTION

The present invention relates generally to the field of bioresorbable packing and stents, and more specifically to a flexible bioresorbable foam, useful for post-operative or drug delivery use, having both hemostatic properties.

BACKGROUND OF THE INVENTION

Various types of sterile packing and stents are used in the medical and surgical fields for keeping tissues apart or preventing adhesion. Such uses include, but are not limited to, nasal packing and sinus stents, packing for inner ear surgery, tympanoplasty, exostosis, orbital decompression, as well as various orifice restenosis prevention uses. Personal uses such as tampons, bandaging and the like also involved sterile packing materials.

Such packing and stents have been made from gauzes, microfibers, nonfibrous expandable packing, such as tampons, and the like. Resorbable packing and stent devices have also been developed. Such packing materials have typically included hyaluronic acid (HA), or salts of hyaluronic acids, which are naturally occurring mucopolysaccharides found in various body fluids and connective tissues. Thus, HA is biocompatible. It has been adapted for use as a surgical aid to prevent tissue contact and adhesion formation. Crosslinking has created somewhat insoluble HA materials. Further, other biocompatible materials such as polysaccharides, especially methylcellulosic materials have been combined with the hyaluronic acid to produce packing materials which are resorbable but are also insoluble and have a longer in-vivo residence time before they dissolve into gels and are absorbed by the body tissues. These materials also have increased fluid absorption capabilities.

Collagen is also known for use in the medical field; it is a major protein constituent of connective tissue and is widely used in medical and surgical applications such as sutures, grafts and surgical prostheses. Typical sources include calf-skin, bovine Achilles tendons, cattle bones, porcine tissue, human cadaver tissue, and rat tails. Collagen, as an animal protein, is bioresorbable, even when crosslinked to reasonable levels. Collagen is available in a variety of forms including powders and fibrils, and in aqueous solution. Collagen may be provided in insoluble or soluble forms.

It has now been discovered that a flexible bioresorbable foam for packing, post-operative use, and other medical uses may be created having both hemostatic properties and a resorption time of about 14 days (also known as an in-vivo residence time). The foam is formed from carboxymethylcellulose (CMC).

SUMMARY OF THE INVENTION

The invention provides a flexible bioresorbable foam having hemostatic properties. More specifically, the invention provides a flexible bioresorbable foam having hemostatic properties comprising carboxymethylcellulose (CMC). The foam is preferably formed primarily from carboxymethylcellulose.

In one embodiment, the invention provides a flexible bioresorbable foam having hemostatic properties consisting essentially of carboxymethylcellulose.

In another embodiment, the invention provides a flexible bioresorbable foam having hemostatic properties consisting of one hundred percent (100%) carboxymethylcellulose.

The invention also provides a medical device wherein said device is a stent intended for insertion between two tissue surfaces of a patient to control bleeding and prevent adhesion. The medical device can be a stent intended for insertion into body cavities and/or orifices such as the eye, ear, nose, throat, anal or vaginal orifices and the like.

One embodiment of the invention also provides a drug delivery and release device for implantation within the body comprising a drug and a flexible bioresorbable foam having hemostatic properties consisting essentially of carboxymethylcellulose.

In another embodiment, the invention is a medical device comprising a carboxymethylcellulose flexible bioresorbable foam having hemostatic properties consisting of one hundred percent (100%) carboxymethylcellulose.

In another embodiment the invention provides a method of making flexible bioresorbable foam having hemostatic properties comprising the steps of:

a) providing a carboxymethylcellulose component,
b) mixing with water to form a suspension;
c) freezing and lyophilizing the carboxymethylcellulose at 0° C. or below;
d) crosslinking and sterilizing said carboxymethylcellulose by means of dry heat to form a flexible crosslinked product.

In alternative embodiments, the foam may also be crosslinked and/or sterilized by use of gamma and ebeam irradiation.

These terms when used herein have the following meanings.

1. The term "bioresorbable" as used herein, means capable of being absorbed by the body.
2. The term "hemostat" means a device or material which stops blood flow.
3. The term "stent" means a material or device used for separating tissue and holding it in such separated position.
4. The term "lyophilizing" means freeze-drying.
5. The term "resorption time" and "in-vivo residence time" are used interchangeably, and refer to the time between insertion into the body and the time at which the material has been substantially completely absorbed into the tissues.
6. The term "adhesion" as used herein, refers to the sticking together of tissues which are in intimate contact for extended periods.
7. The term "dehydrothermal crosslinking" means crosslinking accomplished by application of high temperatures and/or low pressures to a material.

DETAILED DESCRIPTION OF THE PREFERRED EMBODIMENTS

The following detailed description describes certain embodiments and is not to be taken in a limiting sense. The scope of the present invention is defined by the appended claims.

The bioresorbable hemostatic packing provided herein may be used in any manner in which sterile packing and/or stents are normally used in the surgical or medical fields, including uses for which control of low volume bleeding and adhesion prevention are important. Such uses include, but are not limited to, nasal packing and sinus stents, packing for inner ear surgery, tympanoplasty, exostosis, orbital decompression, as well as various orifice restenosis prevention uses.

The packing materials may also be used as single or combination drug delivery systems for humans or mammals.

Bioresorbable foams of the invention are formed primarily from carboxymethylcellulose. Carboxymethylcellulose is a polyanionic polysaccharide, that is, a polysaccharide containing more than one negatively charged group. Carboxymethylcellulose (CMC) is a derivative of cellulose formed by its reaction with alkali and chloroacetic acid. The CMC structure is based on the β-(1→4)-D-glucopyranose polymer of cellulose. Different preparations may have different degrees of substitution, but it is generally in the range 0.6-0.95 derivatives per monomer unit. Carboxymethylcellulose is flexible and soft for ease of handling and contouring within a body cavity, and exhibits the necessary degrees of hydration and expansion to prevent adhesions from forming inside a bodily cavity or in treated bodily tissues. The carboxymethylcellulose expands to at least about 150% of its original dimensions, preferably at least about 200% of its original dimensions.

In one embodiment the bioresorbable foam of the invention is formed from one hundred percent carboxymethylcellulose.

The in-vivo residence times of flexible foams of the invention are typically about 14 days; in many applications, the desirable embodiment of the foam will have an in-vivo residence time of from about 3 days to about 14 days. The in-vivo residence time may be varied as desired by controlling the concentration of the solution used as well as controlling the amount of crosslinking and/or chain scission when forming the carboxymethylcellulose foam.

The foams of the invention are formed by a method which includes formation of a suspension in water. The suspension is formed by mixing with conventional mixers until suspended, being careful to remove large agglomerations. The suspension is mixed, typically at shear rates of from about 0.25 minutes/liter to about 3.0 minutes/liter, and at a speed of from about 7,000 rpm to about 10,000 rpm for processing efficiency. The suspension is then metered into lyophilization trays with a series of cavities. Typical trays have cavities nominally about 6.0 cm by 1.5 cm by 1.0 cm. The suspended solution is then freeze-dried into solid foam blocks using well known procedures involving vacuum conditions at temperatures which are less than the freezing temperature of water, i.e., less than 0° C. After 0° C. is reached, the temperature is then reduced further over time, and cycled; e.g., the temperature is reduced by a few degrees then maintained at the lower temperature for a period of time, and then reduced again. Finally, the temperature reaches a low of about −45° C. where it is maintained for the period required to complete the lyophilization, e.g., at least about 10 hours, and perhaps as much as 24-30 hours. The drying portion of the lyophilization is performed at a vacuum set point in a range from about 10 to about 500 mm of mercury. In one process, the vacuum set point is about 75 mm of mercury (Hg), with the temperature being raised in a controlled fashion. In one process, the temperature is maintained at 0° C. for at least about 2 hours, and up to about 6 hours, then raised to at least about 25° C. to a period of from about 4 hours to about 40 hours.

Upon completion of lyophilization, the foam is then ready to be crosslinked. Crosslinking may be accomplished by dehydrothermal crosslinking, or by exposure to a chemical crosslinking agent. In dehydrothermal crosslinking, the foam is dehydrated to reduce the moisture content to the temperature at which crosslinking occurs, typically to less than about 1%. The product is subjected to elevated temperatures and/or vacuum conditions until crosslinking occurs. Useful combinations of such conditions include vacuum of at least about $10^{-5}$ mm of mercury, and temperatures of at least about 35° C. Naturally, if vacuum is not used, much higher temperatures are required, e.g., above 75° C. The conditions are maintained for at least about 10 hours, typically for about 24 hours until the desired molecular weight has been achieved.

Effective crosslinking can be accomplished by exposure to temperatures of about 115° C. to about 125° C. for periods of about three (3) to about four (4) hours. Sterilization typically occurs after exposure of about three (3) to about four (4) hours at 160° C. or for periods of from about 24 hours to about forty (40) hours at a temperature of about 125° C.

If chemical crosslinking is desired, useful chemical crosslinking agents include aldehydes, e.g., formaldehyde vapor, which can be used by pumping it into a container or a room containing the lyophilized foam and allowed to contact the foam for at least about 2 hours, preferably at least about 5 hours. After the desired exposure time is complete, the crosslinking agent is evacuated from the container or room.

The bioresorbable foam of the invention can be easily handled either wet or dry and may be squeezed, and/or cut to required size. The foam will contour to the body cavity or wound as required, and provides mechanical/chemical hemostasis as well as preventing adhesion, and minimizing swelling and edema.

Although specific embodiments have been illustrated and described herein for purposes of description of the preferred embodiment, it will be appreciated by those of ordinary skill in the art that a wide variety of alternate and/or equivalent implementations calculated to achieve the same purposes may be substituted for the specific embodiments shown and described without departing from the scope of the present invention. Those with skill in the chemical, mechanical, biomedical, and biomaterials arts will readily appreciate that the present invention may be implemented in a very wide variety of embodiments. This application is intended to cover any adaptations or variations of the preferred embodiments discussed herein. Therefore, it is manifestly intended that this invention be limited only by the claims and the equivalents thereof.

What is claimed is:

1. A method of making a flexible bioresorbable foam comprising the steps of:
   a) providing a carboxymethylcellulose component,
   b) mixing the carboxymethylcellulose component with water to form a suspension;
   c) freezing and lyophilizing the blend at 0° C. or below;
   d) crosslinking and sterilizing with dry heat to form a crosslinked product;
   e) performing chain scission on the crosslinked product; and
   f) adjusting the crosslinking chain scission to provide the flexible bioresorbable foam with a selected in-vivo residence time that is between about 3 days and about 14 days, wherein the flexible bioresorbable foam consists essentially of carboxymethylcellulose.

2. A method of making a flexible bioresorbable foam according to claim 1 wherein said flexible bioresorbable foam expands to at least about 150% of an initial volume of the carboxymethylcellulose.

3. A method of making a flexible bioresorbable foam according to claim 2 wherein said flexible bioresorbable foam expands to at least about 200% of an initial volume of the carboxymethylcellulose.

4. A method of making a flexible bioresorbable foam according to claim 1 wherein said in-vivo residence time is from about 3 days to about 8 days.

5. A method of making a flexible bioresorbable foam according to claim 1 wherein the suspension is formed from said carboxymethylcellulose at a shear rate of from about 0.25 minutes/liter to about 3.0 mins/liter, and from about 7,000 rpm to about 10,000 rpm.

6. A method of making a flexible bioresorbable foam according to claim 1 wherein said foam is dehydrothermal crosslinked at a temperature of from about 115° C. to about 125° C. for a period of from about three hours to about four hours.

7. A method of making a flexible bioresorbable foam according to claim 6 wherein said foam is dehydrothermal sterilized at a temperature of from about 145° C. to about 160° C. for a period of from about three hours to about four hours.

8. A method of making a flexible bioresorbable foam according to claim 1 wherein said foam is dehydrothermal crosslinked and sterilized at a temperature of from about 125° C. to about 145° C. for a period of from about twenty-four hours to about forty hours.

9. A method of making a flexible bioresorbable foam according to claim 8 wherein said foam is sterilized and molecular chain scission is performed by bombardment with gamma rays or a beam of electrons.

10. A method of making a medical device according to claim 9 wherein said bioresorbable foam consists of one hundred percent carboxymethylcellulose.

11. A method of making a flexible bioresorbable foam composition according to claim 1 wherein said lyophilization is performed no greater than about −40° C.

12. A method of making a flexible bioresorbable foam comprising the steps of:
  a) providing a carboxymethylcellulose component,
  b) mixing the carboxymethylcellulose component with water to form a suspension;
  c) freezing and lyophilizing the blend at 0° C. or below;
  d) crosslinking to form a crosslinked product, and
  e) sterilizing and performing chain scission said product by means of bombardment with gamma rays or a beam of electrons; and
  f) adjusting the crosslinking and the performing chain scission to provide the flexible bioresorbable foam with a selected in-vivo residence time that is between about 3 days and about 14 days, wherein the flexible bioresorbable foam consists essentially of carboxymethylcellulose.

13. A method according to claim 12 wherein said flexible bioresorbable foam is a stent intended for insertion into a cavity or orifice of the body or to separate opposing tissue surfaces of a patient to control bleeding and prevent adhesion.

14. A method according to claim 13 wherein said stent is intended for insertion into the nasal/sinus cavities, otologic cavity, cranial cavity, the thoracic cavity, the abdominal cavity or the pelvic cavity.

15. A method according to claim 14 wherein said stent is intended for insertion into the eye, ear, nose or throat.

16. A drug delivery device for implantation within the body comprising a drug and the flexible bioresorbable foam prepared according to the method of claim 12.

17. A drug delivery device according to claim 16 wherein said foam is formed from one hundred percent carboxymethylcellulose suspension.

* * * * *